(12) United States Patent
Dureus

(10) Patent No.: US 9,180,269 B2
(45) Date of Patent: Nov. 10, 2015

(54) BREATHING MASK AND METHODS THEREOF

(76) Inventor: Paul Erby Dureus, Freehold, NJ (US)

( * ) Notice: Subject to any disclaimer, the term of this patent is extended or adjusted under 35 U.S.C. 154(b) by 707 days.

(21) Appl. No.: 12/579,934

(22) Filed: Oct. 15, 2009

(65) Prior Publication Data

US 2010/0095966 A1 Apr. 22, 2010

Related U.S. Application Data

(60) Provisional application No. 61/105,996, filed on Oct. 16, 2008.

(51) Int. Cl.
*A61M 16/06* (2006.01)

(52) U.S. Cl.
CPC ........... *A61M 16/06* (2013.01); *A61M 16/0683* (2013.01)

(58) Field of Classification Search
CPC . A61M 16/00; A61M 16/0683; A61M 16/06; A61M 16/0605; A61M 16/0666; A61M 2016/0661; A62B 18/00; A62B 18/02; A62B 18/08; A62B 18/084

USPC ............ 128/207.11, 205.25, 207.13, 206.21, 128/200.24, 201.22, 201.23, 203.29, 128/204.18, 206.12, 206.28, 206.24

See application file for complete search history.

(56) References Cited

U.S. PATENT DOCUMENTS

| | | | | |
|---|---|---|---|---|
| 5,509,409 A | * | 4/1996 | Weatherholt | 128/207.18 |
| 5,538,000 A | * | 7/1996 | Rudolph | 128/205.25 |
| 2006/0283460 A1 | * | 12/2006 | Brown et al. | 128/206.24 |
| 2008/0060649 A1 | * | 3/2008 | Veliss et al. | 128/205.25 |
| 2009/0032018 A1 | * | 2/2009 | Eaton et al. | 128/201.22 |
| 2010/0229866 A1 | * | 9/2010 | Sullivan | 128/205.25 |

OTHER PUBLICATIONS

Dictionary.com definition of the term "cushion".*

* cited by examiner

*Primary Examiner* — Justine Yu
*Assistant Examiner* — Colin W Stuart
(74) *Attorney, Agent, or Firm* — Michael P. Kochka, Esq.

(57) ABSTRACT

Embodiments of the present invention relate to a breathing mask for alleviating conditions causing sleep apnea and avoiding onset claustrophobia in a patient often caused by a breathing mask. In one embodiment of the present invention, a breathing mask comprises an overhead gear assembly comprising an overhead receptor and a hose attachment connected to the overhead receptor, and a patient interface coupled to a connector tubing and/or valve of the overhead gear assembly, wherein the hose attachment is positioned outside of a line of sight of a user, when the breathing mask is utilized by the user.

13 Claims, 13 Drawing Sheets

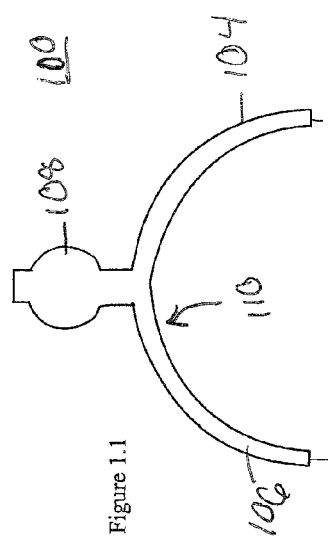
Figure 1.1
Figure 1.2
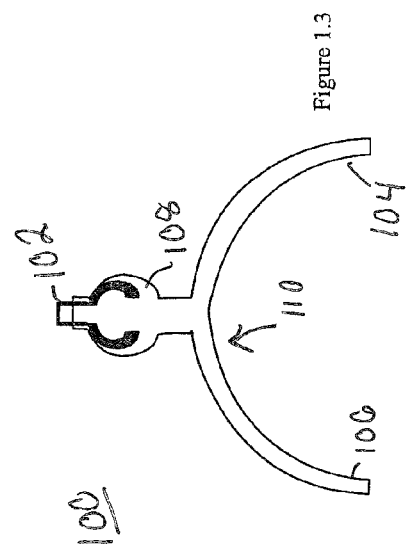
Figure 1.3

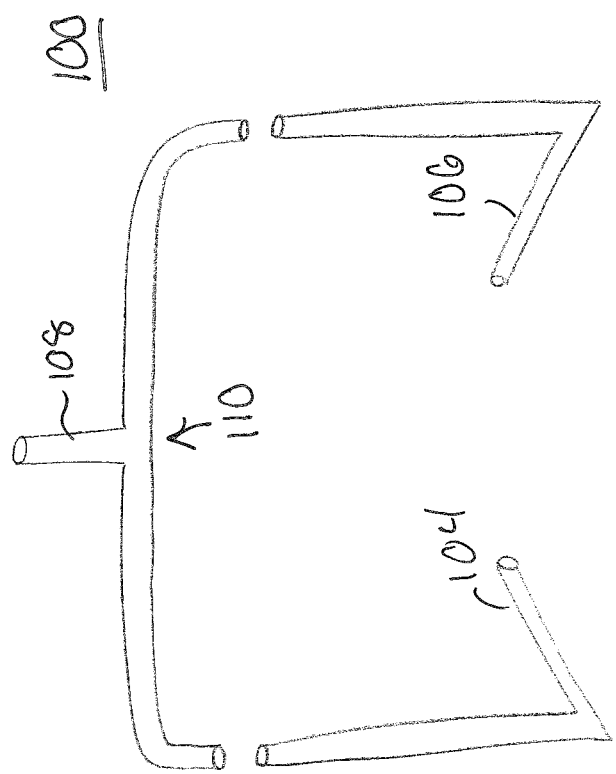
Figure 1.4

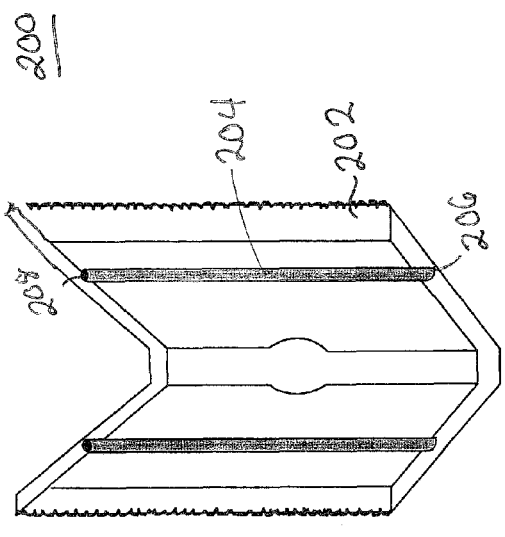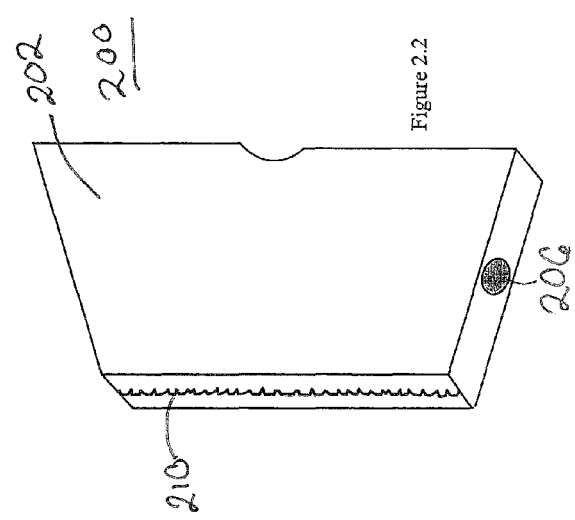
Figure 2.1
Figure 2.2

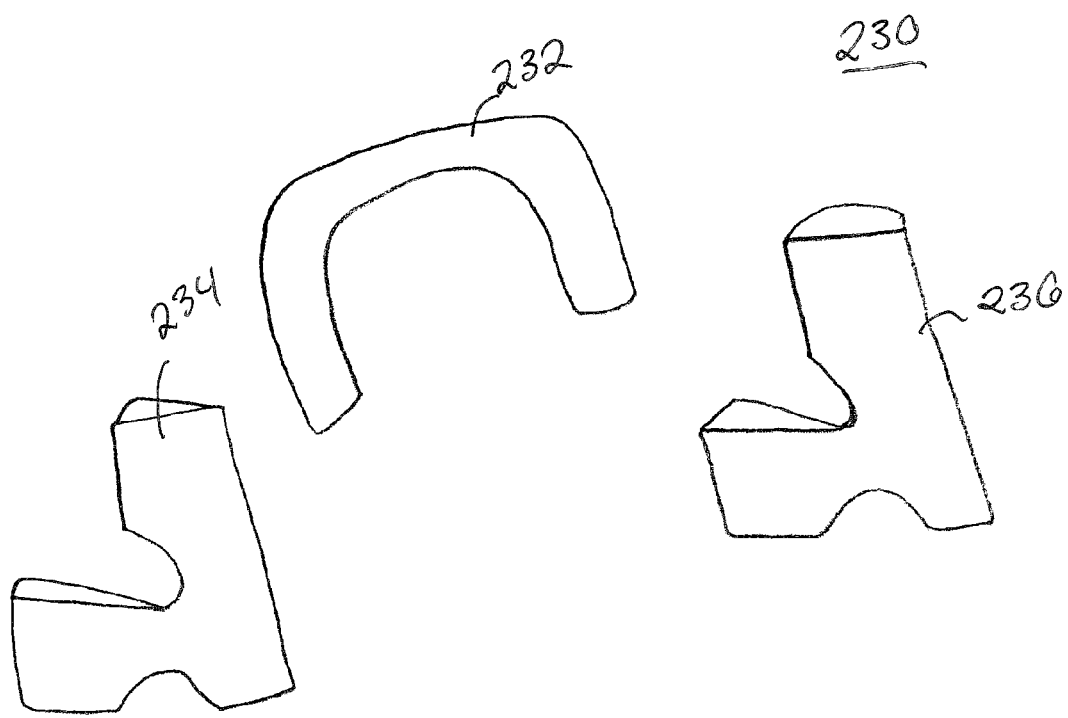
Figure 2.3

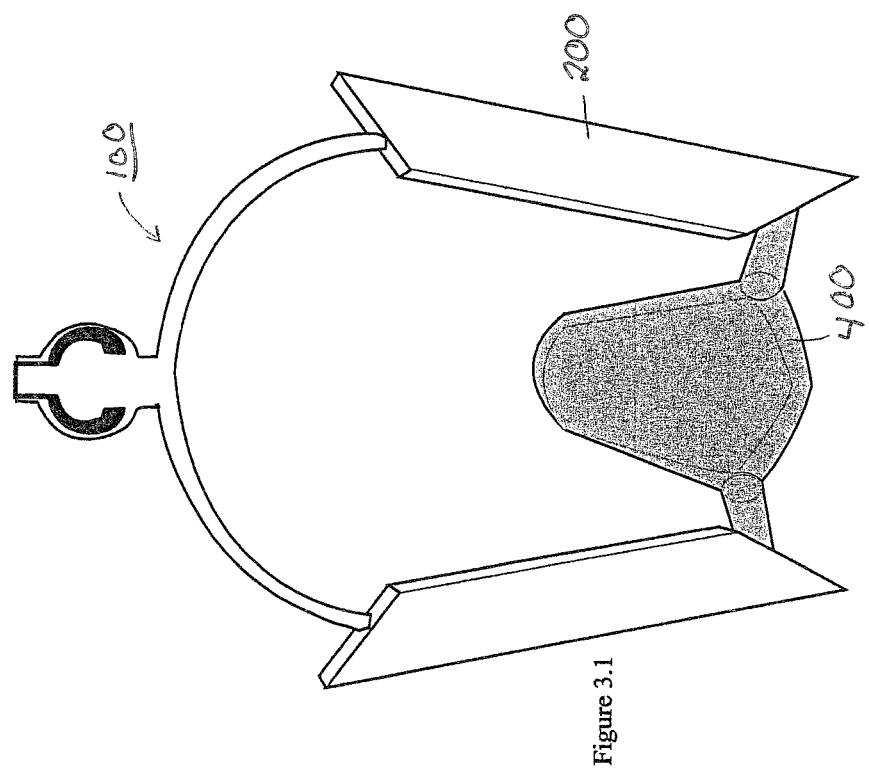
Figure 3.1

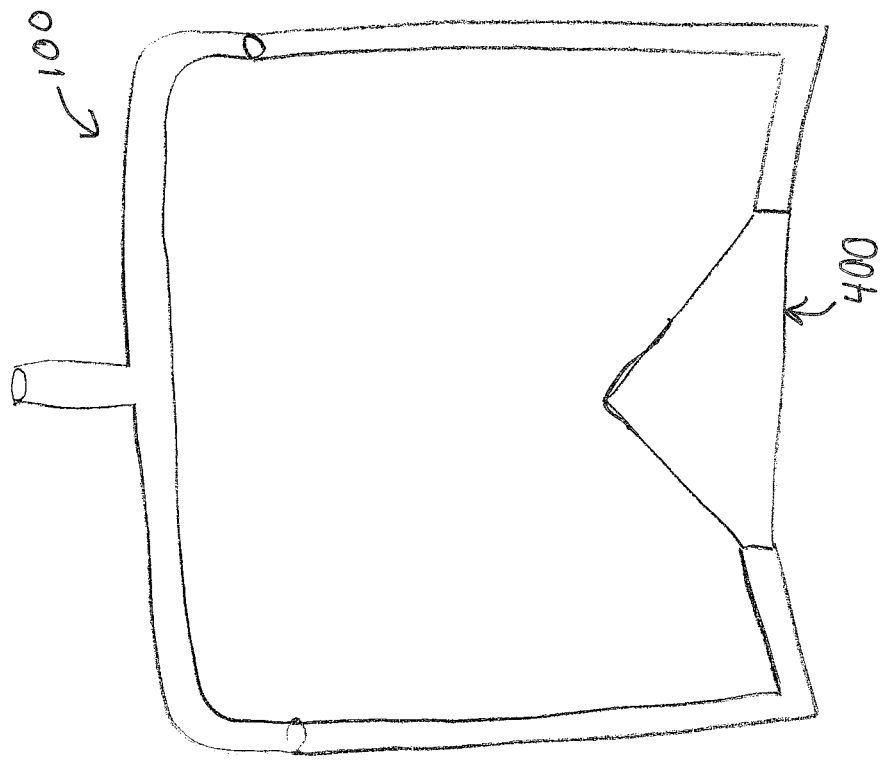
Figure 3.2

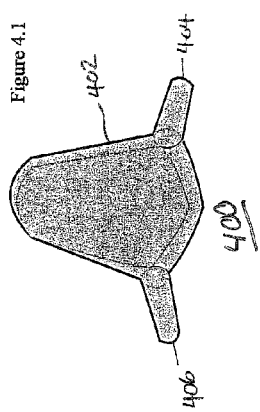
Figure 4.1
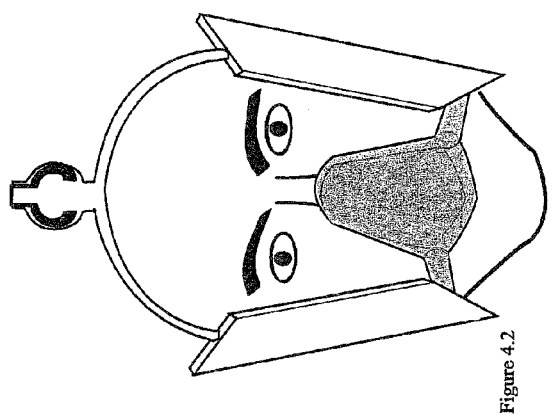
Figure 4.2
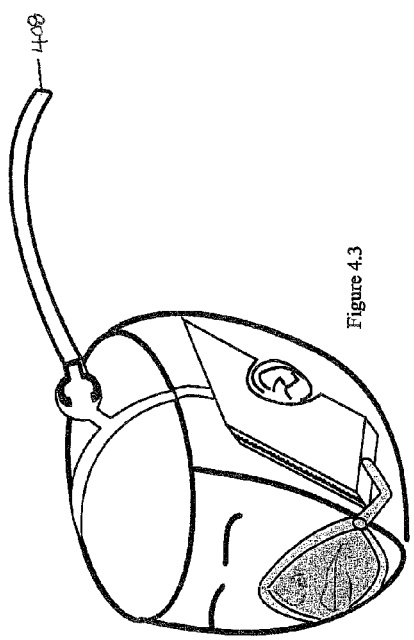
Figure 4.3

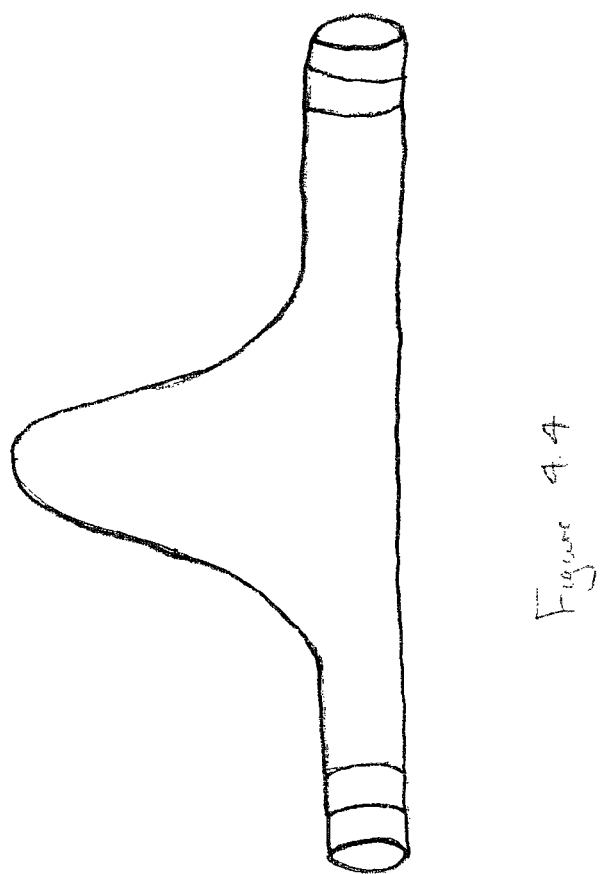
Figure 4.4

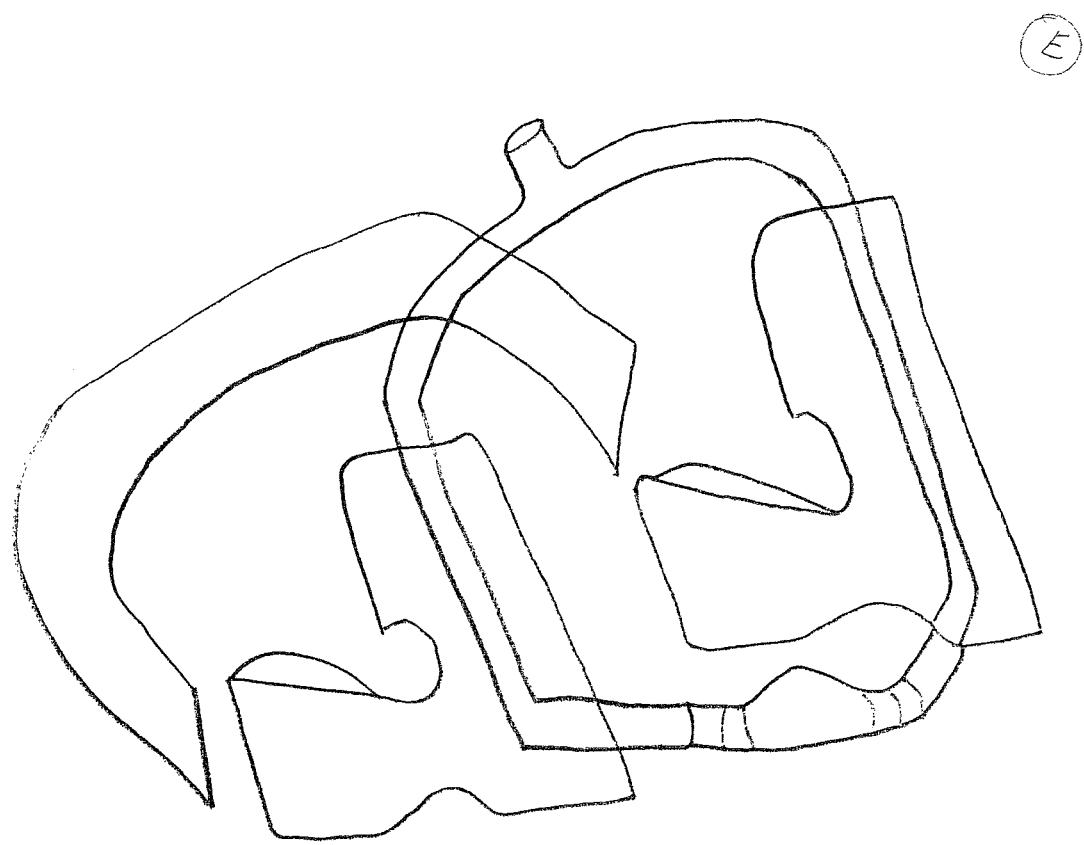
Figure 5.1

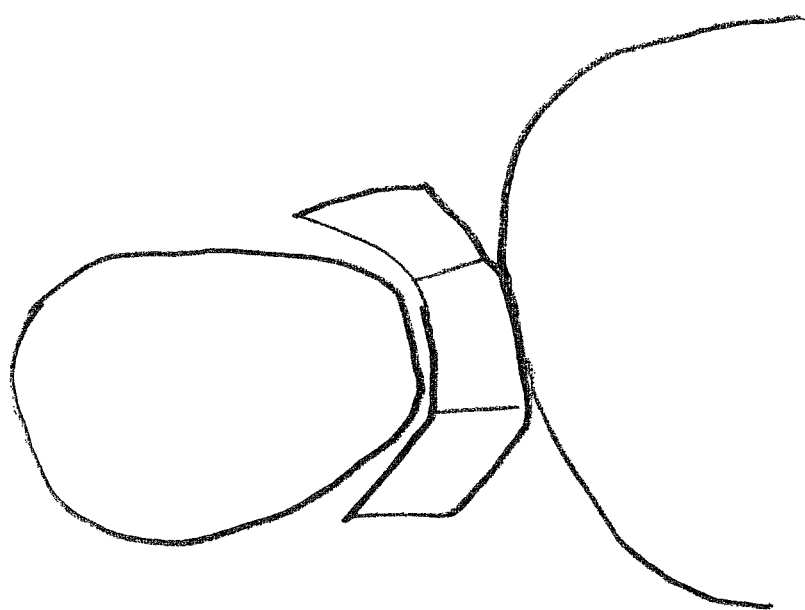
Figure C.2

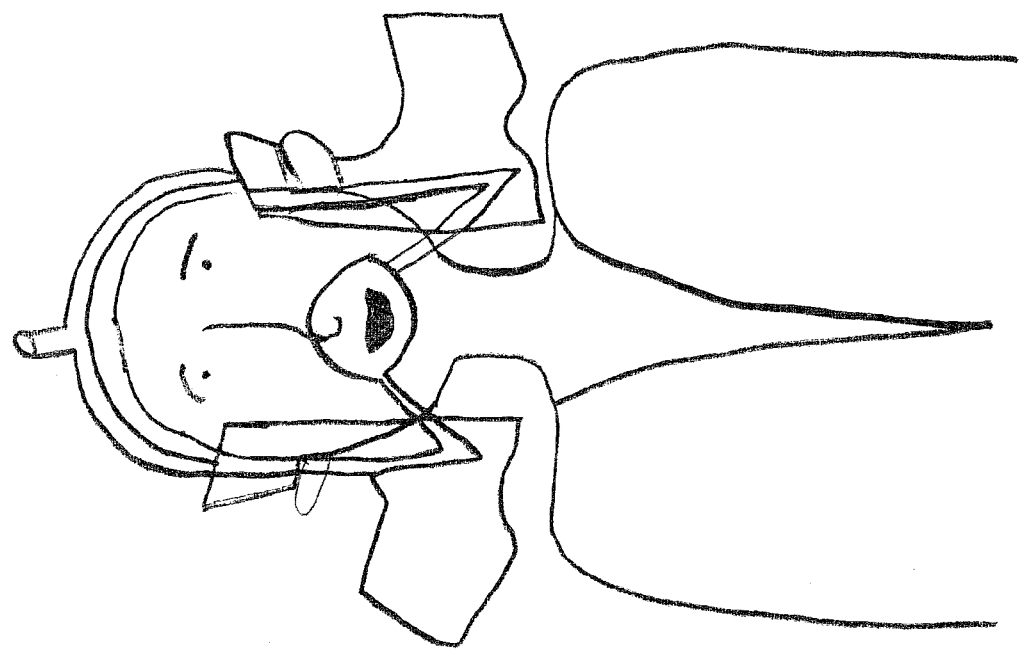
Figure 6.2

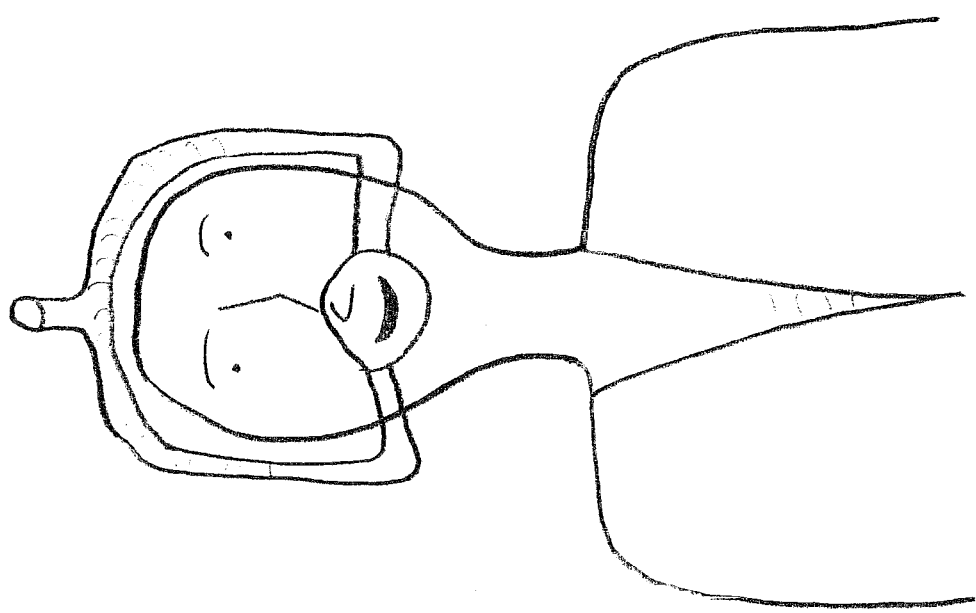

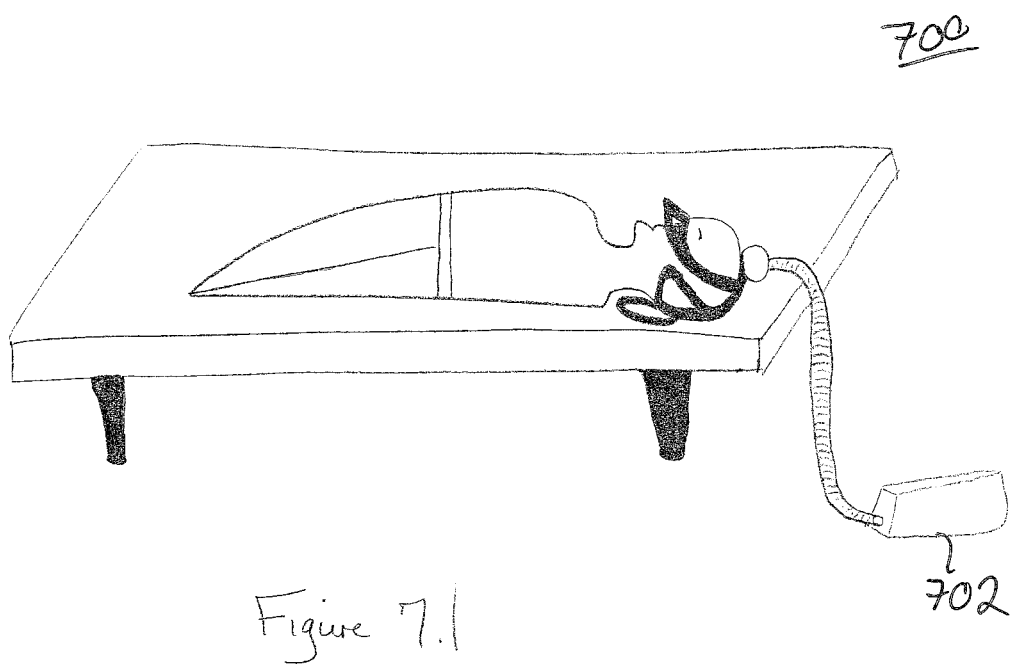
Figure 7.1

BREATHING MASK AND METHODS THEREOF

CROSS-REFERENCE TO RELATED APPLICATIONS

This application claims the benefit of U.S. Provisional Patent Application No. 61/105,996, entitled "Breathing Mask and Methods Thereof," filed Oct. 16, 2008, the entire disclosure of which is incorporated herein by reference in its entirety.

BACKGROUND OF THE INVENTION

1. Field of the Invention

Embodiments of the present invention generally relate to a breathing mask and methods thereof. More specifically, embodiments of the present invention relate to a breathing mask for alleviating conditions causing sleep apnea and avoiding onset claustrophobia in a patient often caused by a breathing mask.

2. Description of the Related Art

Sleep apnea, which manifests itself by intensive snoring during sleep, is a biological disorder in the respiratory channels, in particular the upper air passages which tend to collapse and become blocked towards the end of every exhalation cycle. In order to overcome and avoid suffocation, the patient must exert an effort to continue the breathing process, i.e. the inhalation phase, which effort entails his actual awaking. Patients are thus driven into a serious mental and physical condition, due to accumulated lack of sleep; although the patients seem to be asleep, actually they are not deriving the benefits of slumber, not to mention the inconvenience caused to people in proximity.

In the course of medical research, it has been found that great relief is attained if, by some external means, the patient's lungs (and, of course, the upper bronchial passages included) be kept under a constant, slightly elevated air pressure, above the ambient, "atmospheric" pressure.

In the art of respirators, resuscitators, and the like it is well known to provide apparatus in the form of an enclosure which encompasses a portion of the human body such as the upper torso or thoracic region thereof to provide within the confines of the enclosure a pressure containment chamber wherein pressure variations may be applied to the body to stimulate respiration.

It has been known for some time that sleep apnea can be alleviated through the use of respiratory assist apparatus, such as is used in the well known continuous positive airflow pressure (CPAP) therapy. It is also well recognized that one of the primary causes for patient non-compliance with CPAP or other device therapy is significant physical discomfort cause by the facial masks such devices require.

CPAP therapy essentially requires that air pressure be provided through the patient's nostrils to assist the muscles in the throat to prevent throat blockage during sleep, thus assuaging snoring and actual interruption of breathing. A respirator machine is connected to the patient's nostrils through airflow tubing connected to a facial mask placed over the patient's nose.

There are several known causes of patient concern when prior art apnea therapy masks are in use. For example, physical discomfort can arise with pressure facial neuralgia and vacuum sinusitis. Pressure facial neuralgia is caused by tissue being compressed against the facial bones, for example by a facial mask. Vacuum sinusitis is a painful result of a buildup of pressure in the maxillary cavities located in the maxillary bones located adjacent to the nose. This buildup of pressure is often associated with external pressure placed on the maxillary bones by a facial mask.

What generally goes largely unnoticed, however, in situations where patients have no physical concerns over the use of a mask, significant physiological issues can arise. One major concern is the feeling or sense of claustrophobia when the patient wakes up from a night's sleep and sees a hose coming out of a mask on his/her face.

Thus, there is a need for an improved breathing mask and methods thereof.

SUMMARY OF THE INVENTION

More specifically, embodiments of the present invention relate to a breathing mask for alleviating conditions causing sleep apnea and avoiding onset claustrophobia in a patient often caused by a breathing mask. In one embodiment of the present invention, a breathing mask comprises an overhead gear assembly comprising an overhead receptor and a hose attachment connected to the overhead receptor, and a patient interface coupled to a connector tubing and/or valve of the overhead gear assembly, wherein the hose attachment is positioned outside of a line of sight of a user, when the breathing mask is utilized by the user.

In another embodiment of the present invention, a breathing mask comprises an overhead gear assembly comprising an overhead receptor and a hose attachment to connect the overhead receptor, a patient interface coupled to a connector tubing and/or valve of the overhead gear assembly, and a pillow surrounding at least a portion of the overhead receptor, wherein the hose attachment is positioned proximate to the top of a user's head when worn by the user.

In yet another embodiment of the present invention, a method of administering CPAP treatment to a patient comprises supplying a stream of pressurized air continuously to the patient utilizing a breathing mask, the breathing mask comprising: an overhead gear assembly comprising an overhead receptor and a hose attachment to connect the overhead receptor, and a patient interface coupled to a connector tubing and/or valve of the overhead gear assembly, wherein the hose attachment is positioned outside of a line of sight of the patient when the breathing mask is utilized by the user.

BRIEF DESCRIPTION OF THE DRAWINGS

So the manner in which the above recited features of the present invention can be understood in detail, a more particular description of embodiments of the present invention, briefly summarized above, may be had by reference to embodiments, which are illustrated in the appended drawings. It is to be noted, however, the appended drawings illustrate only typical embodiments of embodiments encompassed within the scope of the present invention, and, therefore, are not to be considered limiting, for the present invention may admit to other equally effective embodiments, wherein:

FIG. 1.1 depicts a frontal view of an overhead receptor in accordance with one embodiment of the present invention;

FIG. 1.2 depicts a perspective view of a mobile head attachment in accordance with one embodiment of the present invention;

FIG. 1.3 illustrates the combination of an overhead receptor and a mobile round head attachment in accordance with one embodiment of the present invention;

FIG. 1.4 illustrates three pieces of a breathing mask in accordance with one embodiment of the present invention;

FIG. 2.1 depicts a cross-sectional view of a pillow model with an internal groove for the placement of the hose in accordance with one embodiment of the present invention;

FIG. 2.2 depicts a lateral view of a pillow model with a closed zipper seal in accordance with one embodiment of the present invention;

FIG. 2.3 illustrates three pieces of a neck support pillow in accordance with one embodiment of the present invention;

FIG. 3.1 illustrates a frontal view of the breathing mask in accordance with one embodiment of the present invention;

FIG. 3.2 illustrates a breathing mask in accordance with one embodiment of the present invention;

FIG. 4.1 illustrates a perspective view of a triangular-shaped mask in accordance with one embodiment of the present invention;

FIG. 4.2 illustrates a frontal view of a breathing mask in accordance with one embodiment of the present invention;

FIG. 4.3 illustrates a side view of the breathing mask in accordance with one embodiment of the present invention;

FIG. 4.4 illustrates a view of a breathing mask in accordance with one embodiment of the present invention;

FIG. 5.1 illustrates a breathing mask in accordance with one embodiment of the present invention;

FIG. 6.1 illustrates a back view of a breathing mask in operation on an individual in accordance with one embodiment of the present invention;

FIG. 6.2 illustrates a front view of a breathing mask having a neck support pillow in operation on an individual in accordance with one embodiment of the present invention;

FIG. 6.3 illustrates a front view of a breathing mask in operation on an individual in accordance with one embodiment of the present invention; and FIG. 7.1 illustrates an individual in a supine position utilizing a breathing mask in operation in accordance with one embodiment of the present invention.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

DETAILED DESCRIPTION

In the following detailed description, numerous specific details are set forth in order to provide an understanding of exemplary embodiments or other examples described herein. In other instances, well-known methods, procedures, and components have not been described in detail, so as to not obscure the following description. Further, the examples disclosed are for exemplary purposes only and other examples may be employed in lieu of, or in combination with, the examples disclosed.

Embodiments of the present invention generally relate to a breathing mask and methods thereof. More specifically, embodiments of the present invention relate to a breathing mask for alleviating conditions causing sleep apnea while avoiding a sense of claustrophobia. In the following, numerous details are set forth in order to provide an understanding of the embodiments or other examples described herein.

FIG. 1.1 depicts a frontal view of an overhead receptor in accordance with one embodiment of the present invention. FIG. 1.2 depicts a perspective view of a mobile head attachment in accordance with one embodiment of the present invention. FIG. 1.3 illustrates the combination of an overhead receptor and a mobile round head attachment in accordance with one embodiment of the present invention. FIG. 1.4 illustrates three pieces of a breathing mask in accordance with one embodiment of the present invention.

In viewing FIGS. 1.1 to 1.4 collectively, the overhead gear assembly 100 as shown includes the overhead receptor 110, a hose attachment 108 and an optional hose retention mechanism 102. The overhead receptor 100 extends to the left and to the right with connector tubing and/or valves 104 and 106 at each end for connection with a breathing mask (not shown). The overhead receptor 110 may be adjustable depending on the size of the patient's head. The hose attachment 108 gives a hose mobility to allow for the patient to move freely from side to side without any discomfort. The hose retention mechanism 102 may retain the hose (not shown) in the hose attachment 108, to ensure the hose will be in a ponytail position atop the patient's head, or alternatively, in a position away from the patient's face to retain the patient's ability to move freely from side to side without the patient feeling suffocated or claustrophobic.

One significant advantage of this assembly provides that the individual is able to move freely throughout the night while the mask and overhead gear assembly is left in place. The hose attachment 108 may generally connect to a blower (not shown), or other air/oxygen source. The connector tubing and/or valves 104 and 106 at the ends of the overhead receptor 110 generally attach to a breathing mask frame (not shown).

In operation, before sleeping, a user places the breathing mask apparatus on his/her head so that the hole in the apparatus through which air is transferred is placed directly over the user's nasal passages. The blower (not shown) is then activated, producing a positive air pressure on the user's airways by forcing air into the user's nasal passages, thus keeping them open throughout the night and increasing the ease of breathing which is hindered by obstructive sleep apnea. The amount of air pressure provided by the blower may be adjusted by the user and may be set to comply with the advice of a medical practitioner or health care specialist.

As appreciated by embodiments of the present invention, acceptable materials for components of the present invention may comprise any suitable material as understood by those of ordinary skill in the art. More specifically, acceptable materials may comprise any material recognized by government agencies monitoring medical or health devices, including the Food and Drug Administration (FDA), the Center for Disease Control (CDC), the Environmental Protection Agency (EPA. Generally, embodiments of the present invention may comprise any polymer, metal, fabric, or the like, as commonly used by hospitals and/or medical device manufacturers.

FIG. 2.1 depicts a cross-sectional view of a pillow model with an internal groove for the placement of the hose in accordance with one embodiment of the present invention. FIG. 2.2 depicts a lateral view of a pillow model with a closed zipper seal in accordance with one embodiment of the present invention. FIG. 2.3 illustrates three pieces of a neck support pillow in accordance with one embodiment of the present invention.

In FIGS. 2.1 through 2.3, collectively, a pillow model 200 may be used to protect and support the patient's face for greater comfort. The pillow model 200 generally comprises a pillow 202 having an internal groove 204 for the placement of the hose (not shown) connected to an overhead gear assembly 100. The internal groove 204 allows for the hose to remain away from the patient's face to relieve the patient from feeling suffocated or claustrophobic. As shown in FIG. 2.2, according to one embodiment of the invention, the pillow model 200 may additionally comprise a fastening mechanism 210, which may include at least one or a combination of a zipper, a set of interlocking snaps, buttons, Velcro®, or any other closure mechanism which is feasible in the context of the present invention. The closure mechanism may optionally be resealable to provide for user adjustment of the hose and to seal the hose within the pillow 210.

In many embodiments of the pillow model 200 are two openings 206 and 208. Opening 208 may be adapted for the portion of the hose connected to the blower (not shown) via overhead gear assembly 100 and opening 206 is for the portion of the hose connected to the patient interface (not shown). The pillow model 200 may be made of a cushion-like or absorbent material, such as foam, cotton, down feathers or the like, and is adjustable to different temperatures to accommodate each patient's needs. FIG. 2.3 illustrates three pieces of a neck support pillow in accordance with yet another embodiment of the present invention. The neck support pillow 230, having a back section 232 and two side sections 234 and 236, may be used concurrently with the pillow model 200 as may provide increased patient comfort and/or mobility.

FIG. 3.1 illustrates a frontal view of the breathing mask assembly in accordance with one embodiment of the present invention. In accordance with embodiments of the present invention, the patient interface 400 may be a full-face mask, nasal mask, nasal pillow or the like. As depicted in the exemplary embodiment of FIG. 3.2, the patient interface 400 comprises a full-face breathing mask. The patient interface may be an industry-standard, substantially-triangular face mask, connected to the overhead gear assembly 100 using a pillow model 200.

FIG. 4.1 illustrates a front view of a substantially triangular face mask as a patient interface, in accordance with one embodiment of the present invention. In accordance with embodiments of the present invention, the breathing mask may be positioned around the nose and mouth as shown in FIG. 4.2. The mask may include a mask cushion (not shown), a hollow body (not shown) and a cushion clip (not shown), as is common for face masks in the industry. As shown, the patient interface 400 generally comprises a breathing portion 402, an inflow air pathway 404 and an outflow air pathway 406.

FIG. 4.3 depicts a pillow model breathing mask assembly in use on a patient, in accordance with one embodiment of the present invention. The pillow model 200 may generally be positioned on a patients face comfortably, for example, by leaving room for the patient's ear, thus ensuring greater patient comfort.

A hose 408 may generally be attached to the hose attachment 108 atop the patient's head, outside of the patient's view. In many embodiments of the present invention, by keeping the hose 408 out of the patient's view, there is minimal likelihood the patient will awake during the night and immediately feel claustrophobic, or a similar fear, due to the hose or tubes entering the patient interface.

Optionally, in accordance with one embodiment of the present invention, a neck support pillow 230 may be installed in the apparatus to enhance the overall comfort level of the patient utilizing the apparatus. FIG. 4.4 illustrates a view of a breathing mask in accordance with one embodiment of the present invention. As shown in FIG. 4.4, in accordance with one embodiment of the present invention, the breathing mask may cover only the nasal region of the user, thus leaving the oral region exposed.

FIG. 5.1 depicts a breathing mask assembly in accordance with one embodiment of the present invention. In accordance with one embodiment of the present invention, the breathing mask assembly may comprise overhead gear assembly 100, a patient interface 400 and a neck support pillow system 230.

FIG. 6.1 illustrates a back view of a breathing mask in operation on an individual in accordance with one embodiment of the present invention. FIG. 6.2 illustrates a front view of a breathing mask assembly having a neck support pillow in operation on an individual in accordance with one embodiment of the present invention. FIG. 6.3 illustrates a front view of a breathing mask assembly in operation on an individual in accordance with one embodiment of the present invention. Viewing these three figures collectively, a breathing mask assembly in accordance with one embodiment of the present invention may include a breathing mask and a neck pillow support portion.

FIG. 7.1 illustrates a patient in a supine position utilizing a breathing mask assembly 700 in accordance with one embodiment of the present invention. The breathing mask may generally be connected to a blower 702, or other air source, for providing the increased air flow to the patient.

While the foregoing is directed to embodiments of the present invention, other and further embodiments of the invention may be devised without departing from the basic scope thereof. In view of the wide variety of embodiments that can be applied, it should be understood that the illustrated examples are exemplary only, and should not be taken as limiting the scope of the following claims. Further, the claims should not be read as limited to the described order or elements unless stated to that effect. In addition, use of the term "means" in any claim is intended to invoke 35 U.S.C. §112, ¶6, and any claim without the word "means" is not so intended.

What is claimed is:

1. A breathing mask comprising:
an overhead gear assembly comprising an overhead receptor and a hose attachment connected to the overhead receptor;
a patient interface; and
a pillow surrounding at least a portion of the overhead receptor, the pillow comprising a back section for supporting a user's neck and two side sections for supporting two opposing sides of the user's head, each of the side sections comprising an internal groove for accepting a tubing, the internal groove embedded in each of the side sections along the entire length of the side sections, the side sections having an outer surface and an inner surface, wherein the outer surface of the side sections is substantially flat and parallel to the inner surface;
wherein the hose attachment is positioned outside of a line of sight of the user, when the breathing mask is utilized by the user;
wherein the breathing bask comprises no structural elements that would contact a forehead of a user when in use; and
wherein the overhead receptor is adapted to be positioned in substantially the center of a top portion of the user's head.

2. The breathing mask of claim 1, further comprising a hose retention mechanism.

3. The breathing mask of claim 1, wherein the pillow further comprises a fastening mechanism to enclose the tubing within each of the grooves of the side sections.

4. The breathing mask of claim 1, wherein the patient interface comprises one of a full-face mask, a nasal mask, or a nasal pillow.

5. The breathing mask of claim 1, further comprising an air source coupled to the hose attachment.

6. A breathing mask comprising:
- an overhead gear assembly comprising an overhead receptor and a hose attachment connected to the overhead receptor;
- a patient interface; and
  - a pillow surrounding at least a portion of the overhead receptor, the pillow comprising two side sections for supporting two opposing sides of a user's head, each of the side sections comprising an internal groove for accepting a tubing, the internal groove embedded in each of the side sections along the entire length of the side sections, the side sections having an outer surface and, an inner surface, wherein the outer surface of the side sections is substantially flat and parallel to the inner surface;
- wherein the hose attachment is positioned proximate to the top of the user's head when worn by the user;
- wherein the hose attachment is positioned outside of a line of sight of the user, when the breathing mask is utilized by the user; and
- wherein the breathing bask comprises no structural elements that would contact a forehead of a user when in use.

7. The breathing mask of claim 6, wherein the patient interface consisting of a full-face mask, a nasal mask, or a nasal pillow.

8. The breathing mask of claim 6, wherein the pillow further comprises a fastening mechanism to enclose the tubing within each of the grooves of the side sections.

9. The breathing mask of claim 6, further comprising an air source coupled to the hose attachment.

10. The breathing mask of claim 6, wherein the patient interface comprises an inflow air pathway and an outflow air pathway.

11. A method of administering CPAP treatment to a patient comprising:
- supplying a continuous stream of pressurized air from an air source to the patient utilizing a breathing mask;
- the breathing mask comprising:
  - an overhead gear assembly comprising an overhead receptor and a hose attachment connected to the overhead receptor;
- a patient interface; and
  - a pillow surrounding at least a portion of the overhead receptor, the pillow comprising two side sections for supporting two opposing sides of a user's head, each of the side sections comprising an internal groove for accepting a tubing, the internal groove embedded in each of the side sections along the entire length of the side sections, the side sections having an outer surface and an inner surface, wherein the outer surface of the side sections is substantially flat and parallel to the inner surface;
- wherein the hose attachment is positioned outside of a line of sight of the patient when the breathing mask is utilized by the patient;
- wherein the breathing mask comprises no structural elements that would contact a forehead of a patient when in use; and
- wherein the overhead receptor is adapted to be positioned in substantially the center of a top portion of the patient's head.

12. The method of claim 11, wherein the breathing mask further comprises a hose retention mechanism.

13. The method of claim 11, wherein the patient interface comprises one of a full-face mask, a nasal mask, or a nasal pillow.

* * * * *